(12) United States Patent
Bamdad et al.

(10) Patent No.: US 10,638,924 B2
(45) Date of Patent: May 5, 2020

(54) LARYNGOSCOPE DEVICE

(71) Applicants: Javid Bamdad, Tabriz (IR); Behzad Abedi, Tabriz (IR); Amir Mahdi Bamdad, Tabriz (IR); Yaghoob Ghasemi, Tabriz (IR)

(72) Inventors: Javid Bamdad, Tabriz (IR); Behzad Abedi, Tabriz (IR); Amir Mahdi Bamdad, Tabriz (IR); Yaghoob Ghasemi, Tabriz (IR)

(*) Notice: Subject to any disclaimer, the term of this patent is extended or adjusted under 35 U.S.C. 154(b) by 56 days.

(21) Appl. No.: 16/001,940

(22) Filed: Jun. 7, 2018

(65) Prior Publication Data

US 2019/0053697 A1     Feb. 21, 2019

(51) Int. Cl.
*A61B 1/267* (2006.01)
*A61B 1/015* (2006.01)
*A61B 1/06* (2006.01)
*A61B 1/00* (2006.01)

(52) U.S. Cl.
CPC .......... *A61B 1/267* (2013.01); *A61B 1/00091* (2013.01); *A61B 1/00094* (2013.01); *A61B 1/00108* (2013.01); *A61B 1/015* (2013.01); *A61B 1/0669* (2013.01); *A61B 1/00105* (2013.01)

(58) Field of Classification Search
CPC ................ A61B 1/267; A61B 1/00108; A61B 2017/00548; A61B 2017/00535
See application file for complete search history.

(56) References Cited

U.S. PATENT DOCUMENTS

| 4,384,570 | A  | * | 5/1983  | Roberts ............... | A61B 1/07  |
|           |    |   |         |                        | 600/185    |
| 5,571,071 | A  | * | 11/1996 | Shapiro ............... | A61B 1/267 |
|           |    |   |         |                        | 600/185    |
| 6,106,458 | A  | * | 8/2000  | Ha ....................... | A61B 1/015 |
|           |    |   |         |                        | 600/187    |
| 6,248,061 | B1 | * | 6/2001  | Cook, Jr. ............. | A61B 1/267 |
|           |    |   |         |                        | 600/187    |
| 2007/0287888 | A1 | * | 12/2007 | Lovell ............... | A61B 1/00094 |
|           |    |   |         |                        | 600/187    |
| 2014/0360494 | A1 | * | 12/2014 | Herskovic ........... | A61M 11/007 |
|           |    |   |         |                        | 128/200.18 |
| 2017/0035284 | A1 | * | 2/2017  | Fadel .................. | A61B 1/267 |

* cited by examiner

*Primary Examiner* — David W Bates

(57) ABSTRACT

A laryngoscope device adapted to suction or delivery of liquid or air to clean particulate materials in larynx, is disclosed. The laryngoscope device, comprises a handgrip with an internal cavity and a container configured to hold fluid or air is disposed within said internal cavity. A blade member is mounted on the handgrip with predetermined length and curvature to insert into an oral cavity. The blade member comprises a tip portion in fluid communication with the container. The tip portion is configured to suction and discharge fluid or air. A lever is attached at a proximal end of the blade member and projects at an angle away from the handgrip. The lever is operable by a user, to execute suction or discharge in the oral cavity via the tip portion. An oxygenation tube is disposed at a distal end of said blade member, for delivering oxygen.

4 Claims, 4 Drawing Sheets

LARYNGOSCOPE DEVICE

BACKGROUND OF THE INVENTION

A laryngoscope is a device used to facilitate intubation for anesthesia, examine larynx or for inserting a tube. During use of this tool, following uncontrollable phenomena occurs. Spontaneous secretion of saliva due to physiological or pathological conditions such as glandular disorder, glandular hyperplasia, infectious disease, etc. This condition is divided into physiologic and pathologic silos or also called as drooling. One condition, referred as anterior drooling, causes saliva to spill out of the oral cavity. Another condition, referred as posterior drooling, causes accumulation of abundant and often thick salivary fluids in the area. Further, existence of salivary secretions in some poisonings, such as organophosphates, makes it difficult to intubate and for suction.

Generally, the presence of salivary gland disorders, or the use of psychedelic or anticholinergic drugs, cause dryness and exudate in the larynx area and causes vision problems during the intubations. Furthermore, trauma of the maxillofacial area or postoperative bleeding in some surgical procedures such as adenoidectomy requiring—intubation makes it difficult to perform intubation. These limitations often confine the performance of the laryngoscope and lead to patient death.

Therefore, there is a need for a simple and efficient laryngoscope device, adapted to suction or delivery of liquid or air to clean particulate materials, facilitate intubation and supply oxygen.

SUMMARY OF THE INVENTION

The present invention provides a laryngoscope device adapted for suction or delivery of liquid or air. The device is configured to clean particulate materials such as blood, saliva in the larynx, facilitates intubation, and supplies oxygen.

According to the present invention, the laryngoscope device comprises a handgrip having an internal cavity. The laryngoscope device further comprise a container and a power source are disposed within the internal cavity. The container is configured to hold fluid or air. In one embodiment, the container is contoured to match the internal dimensions of the internal cavity of the handgrip. A blade member is mounted on the handgrip with predetermined length and curvature to insert into an oral cavity. The blade member comprises a tip portion in fluid communication with the container, configured to suction and discharge of fluid or air, from the container.

A lever attached at a proximal end of the blade member and projects at an angle away from the handgrip. The lever is operable by a user, to execute suction or discharge in the oral cavity via the tip portion. In one embodiment, the lever is adapted to move away from the handgrip to suction liquid or air. In one embodiment, the lever is adapted to move towards the handgrip to deliver liquid or air.

The laryngoscope further comprises an oxygenation tube disposed at a distal end of the blade member, for delivery of oxygen to the airway during laryngoscopy. In one embodiment, the blade member is detachably mounted on the handgrip. In one embodiment, the device further comprises a power source disposed at a base of the cavity portion. In one embodiment, the container is positioned above the power source. In one embodiment, the device further comprises a light source disposed at a distal end of the blade member powered by the power source.

One aspect of the present disclosure is directed to a laryngoscope device, comprising: (a) a handgrip having an internal cavity; (b) a container configured to hold fluid or air, disposed within said internal cavity; (c) a blade member mounted on said handgrip with predetermined length and curvature to insert into an oral cavity, comprising a tip portion in fluid communication with said container configured to suction and discharge fluid or air, from said container; (d) a lever attached at a proximal end of said blade member and projects at an angle away from said handgrip, operable by a user, to execute suction or discharge in the oral cavity, via the tip portion, and (e) an oxygenation tube disposed at a distal end of said blade member, for delivery of oxygen.

In one embodiment, the blade member is detachably mounted on the handgrip. In another embodiment, the laryngoscope device further comprises a power source disposed at a base of the internal cavity. In another embodiment, the laryngoscope device further comprises a light source disposed at a distal end of the blade member powered by the power source. In one embodiment, the lever is adapted to move towards the handgrip to discharge liquid or air. In another embodiment, the lever is adapted to move away from the handgrip to suction liquid or air. In one embodiment, the container is contoured to match the internal dimensions of the internal cavity of the handgrip. In one embodiment, the power source is a battery.

Another aspect of the present disclosure is directed to a laryngoscope device, comprising: (a) a handgrip having an internal cavity; (b) a container configured to hold fluid or air, disposed within said internal cavity; (c) a blade member mounted on said handgrip with predetermined length and curvature to insert into an oral cavity, comprising a tip portion in fluid communication with said container configured to suction and discharge fluid or air, from said container; (d) a lever attached at a proximal end of said blade member and projects at an angle away from said handgrip, operable by a user, to execute suction or discharge in the oral cavity, via the tip portion; (e) an oxygenation tube disposed at a distal end of said blade member, for delivery of oxygen; (f) a power source disposed at a base of said internal cavity, and (g) a light source disposed at a distal end of said blade member powered by the power source.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to a laryngoscope device, and more particularly relates to a laryngoscope device adapted to suction or delivery of liquid or air to clean particulate materials, facilitate intubation and supply oxygen.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
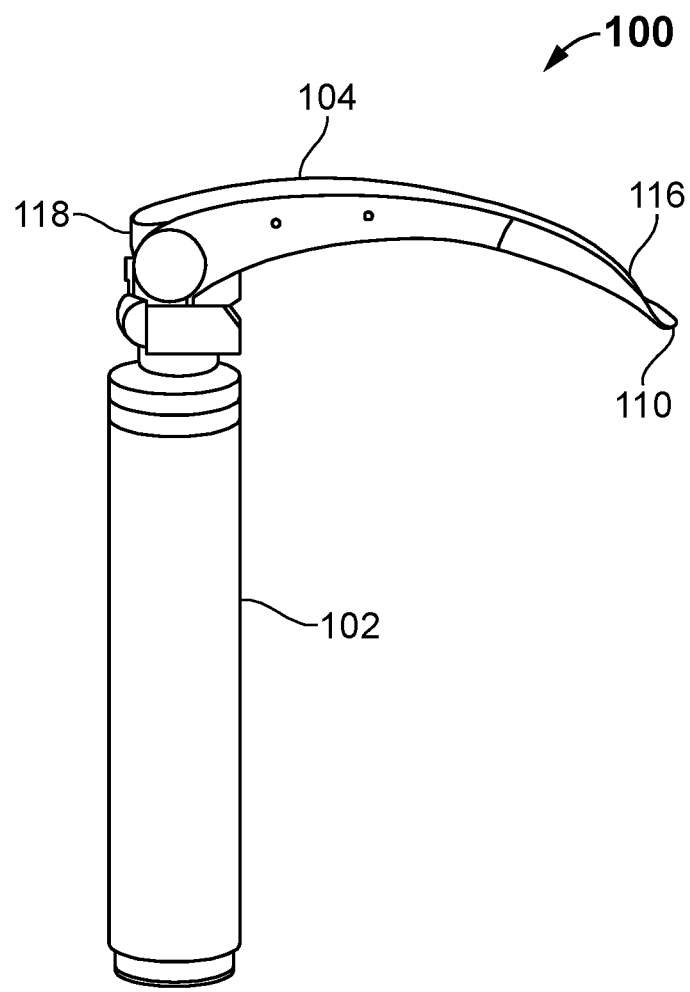
FIG. 1 shows a front perspective view of a laryngoscope device, according to one embodiment of the present invention.
Figure 2:
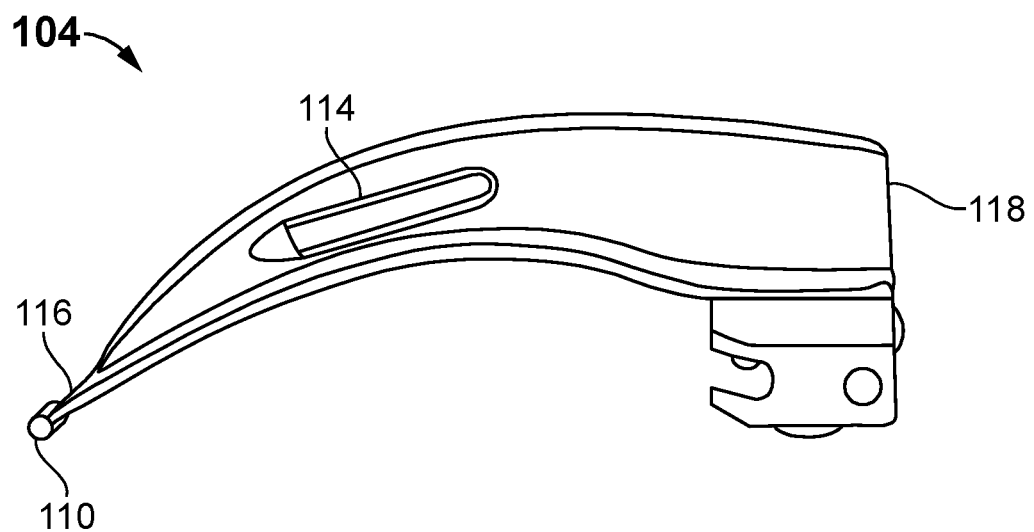
FIG. 2 shows a side view of a blade member of the laryngoscope device, according to one embodiment of the present invention.
Figure 3:
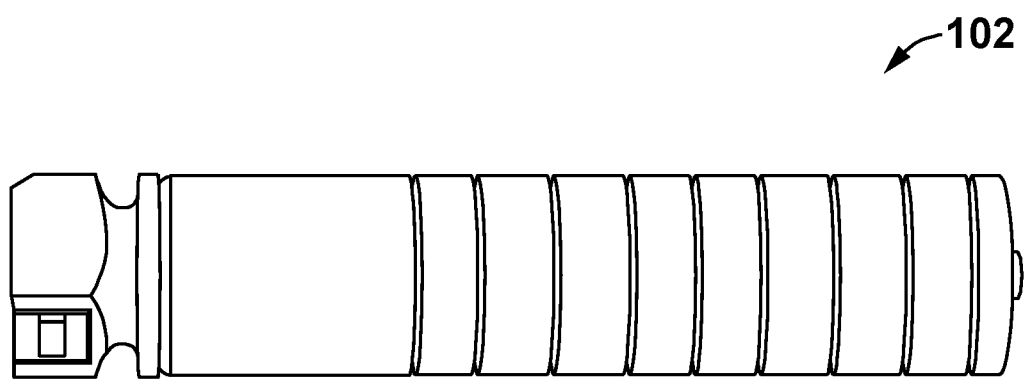
FIG. 3 shows a side view of a handgrip of the laryngoscope device, according to one embodiment of the present invention.

Referring to FIG. 1, a laryngoscope device 100 of the present invention is generally shown. The laryngoscope device 100 comprises a handgrip 102 with an upper end, a lower end, and an internal cavity. The laryngoscope device 100 further comprises a blade member 104 having a distal end 116 and a proximal end 118. The proximal end 118 of the blade member 104 is connected to the upper end of the handgrip 102. In one embodiment, the blade member 104 is detachably connected to the handgrip 102. A side view of the detached blade member 104 of the laryngoscope device 100, according to one embodiment of the present invention is disclosed in FIG. 2. A side view of the handgrip 102 detached from the laryngoscope device 100, according to one embodiment of the present invention is disclosed in FIG. 3.

Figure 4:
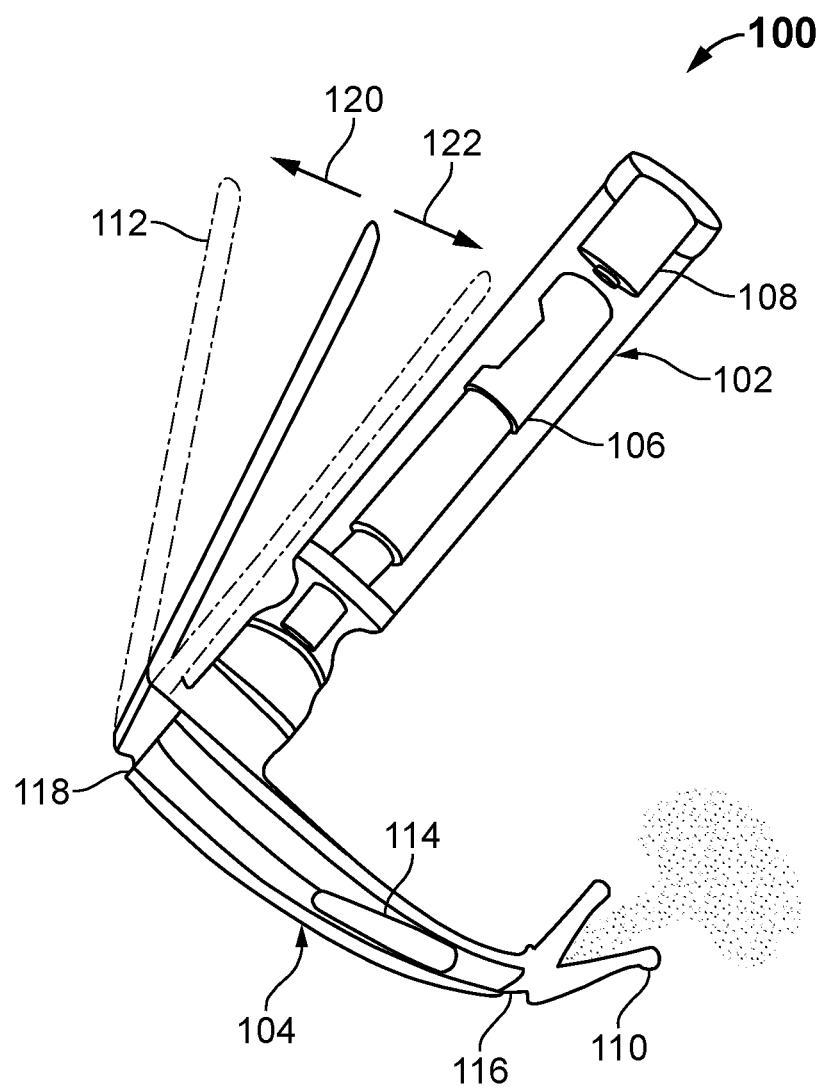
FIG. 4 illustrates suction and discharge operation of the laryngoscope device, according to one embodiment of the present invention.

Referring to FIG. 4, a container 106 is disposed within the internal cavity of the handgrip 102, configured to hold fluid or air. In one embodiment, the container 106 is contoured to match the internal dimensions of the internal cavity of the handgrip 102. The blade member 104 comprises a predetermined length and curvature to insert into an oral cavity. Referring to FIGS. 1-4, the blade member 104 comprises a tip portion 110 in fluid communication with the container 106. In one embodiment, the container 106 comprises a liquid or air, to spray/deliver and suction the liquid or air at the larynx, thereby cleaning the blood, or other waste materials from the pathway and facilitates in intubation of anaesthesia and also removes any obstacle that confines the eyesight of the user or physician examining the larynx.

In one embodiment, the device 100 further comprises a lever 112, attached at a proximal end 118 of the blade member 104 and projects at an angle away from the handgrip 102. The lever 112 is operable by a user, to execute suction or discharge in the oral cavity via the tip portion 110. In one embodiment, the lever 112 is adapted to move away from the handgrip 102 to suction liquid or air. In one embodiment, the lever 112 is adapted to move towards the handgrip 102 to deliver liquid or air. In one embodiment, on pressing the lever 112 by the user towards the handgrip 102, represented by arrow 122, causes the tip portion 110 to separate and discharge the liquid or air. In one embodiment, on pressing the lever 112 by the user away from the handgrip 102, represented by arrow 120, causes the tip portion 110 to separate, and suction liquid or waste from the larynx of the patient.

In one embodiment, the power of suction is high, such that to prevent entry of liquid into the lungs. In another embodiment, the intensity of the spray or suction operation of the laryngoscope device 100 is adjustable based on an anatomical difference between patients such as male, female or child. The laryngoscope device 100 further comprises an oxygenation tube 114 disposed at a distal end 116 of the blade member 104, to deliver oxygen. During laryngoscopy, the concurrent delivery of oxygen to the patient's trachea allows the physician to elevate the glottis to view vocal cord for placement of the endotracheal tube, prevents hypoxia and allows to perform other critical tasks.

The laryngoscope device 100 further comprises a power source 108 disposed within a base of the internal cavity of the handgrip 102. The laryngoscope 100 further comprises a light source disposed at the distal end 116 of the blade member 104. The light source is operatively coupled to the power source 108 at the base of the handgrip 102. In one embodiment, the power source 108 is a battery. In one embodiment, the power source 108 is a rechargeable battery. The light source provides light from the distal end 116 of the laryngoscope device 100 and, to a degree, illuminates the mouth of the patient. The illumination of light source down the throat of a patient, further provides, line of sight to the physician performing the laryngoscopy.

Advantageously, the present invention enables to suction or delivery of liquid or air to clean particulate materials such as blood, saliva in the larynx. The laryngoscope device 100 further facilitates intubation, and supplies oxygen. The light source enables the user to conveniently check the patient's throat.

One aspect of the present disclosure is directed to a laryngoscope device. The device comprises a handgrip having an internal cavity, a container configured to hold fluid or air, disposed within said internal cavity, and a blade member mounted on said handgrip with predetermined length and curvature to insert into an oral cavity, comprising a tip portion in fluid communication with said container configured to suction and discharge fluid or air, from said container. The laryngoscope device may further comprise a lever attached at a proximal end of said blade member and projects at an angle away from said handgrip, operable by a user, to execute suction or discharge in the oral cavity, via the tip portion. Further, the laryngoscope device may further comprise an oxygenation tube disposed at a distal end of said blade member, for delivery of oxygen.

The blade member may be detachably mounted on the handgrip. The laryngoscope device may further comprise a power source disposed at a base of the internal cavity. The laryngoscope device may further comprise a light source disposed at a distal end of the blade member powered by the power source. The clamp maybe adapted to move towards the handgrip to discharge liquid or air, and/or the lever may be adapted to move away from the handgrip to suction liquid or air. The container may be contoured to match the internal dimensions of the internal cavity of the handgrip. It is possible for a battery to act as the power source for the device.

Another aspect of the present disclosure is directed to a laryngoscope device, comprising a handgrip having an internal cavity; a container configured to hold fluid or air, disposed within said internal cavity; a blade member mounted on said handgrip with predetermined length and curvature to insert into an oral cavity, comprising a tip portion in fluid communication with said container configured to suction and discharge fluid or air, from said container; and a lever attached at a proximal end of said blade member and projects at an angle away from said handgrip, operable by a user, to execute suction or discharge in the oral cavity, via the tip portion. The laryngoscope device may further comprise an oxygenation tube disposed at a distal end of said blade member, for delivery of oxygen, as well as a power source disposed at a base of said internal cavity. A light source may be disposed at a distal end of said blade member and this can be powered by the power source such as a battery, for example.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions.

Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

What is claimed is:

1. A laryngoscope device, comprising:
a handgrip having an internal cavity;
a container configured to hold fluid or air, disposed within said internal cavity;
a blade member mounted on said handgrip with predetermined length and curvature to insert into an oral cavity, comprising a tip portion at a distal end of said blade member in fluid communication with said container configured to suction and discharge fluid or air, from said container;
a lever attached at a proximal end of said blade member and projects at an angle away from said handgrip, operable by a user, wherein the lever is adapted to move towards the handgrip to discharge the liquid or the air from the container into the oral cavity, via the tip portion at a distal end of said blade member;
wherein the lever is adapted to move away from the handgrip to suction liquid or air;
an oxygenation tube disposed at a distal end of said blade member, for concurrent delivery of oxygen to a patient's trachea from a separate oxygen supply;
a power source disposed at a base of said internal cavity, and
a light source disposed at a distal end of said blade member powered by the power source.

2. The laryngoscope device of claim 1, wherein the blade member is detachably mounted on the handgrip.

3. The laryngoscope device of claim 1, wherein the container is contoured to match the internal dimensions of the internal cavity of the handgrip.

4. The laryngoscope device of claim 1, wherein the power source is a battery.

* * * * *